United States Patent [19]

Caprioli

[11] Patent Number: 5,572,023
[45] Date of Patent: Nov. 5, 1996

[54] ELECTROSPRAY METHODS AND APPARATUS FOR TRACE ANALYSIS

[75] Inventor: Richard M. Caprioli, Houston, Tex.

[73] Assignee: Board of Regents, The University of Texas System, Austin, Tex.

[21] Appl. No.: 453,385

[22] Filed: May 30, 1995

[51] Int. Cl.[6] .................................................. H01J 49/10
[52] U.S. Cl. .................... 250/288; 250/281; 250/282
[58] Field of Search ............................ 250/288, 288 A, 250/281, 282, 423 R, 429, 425

[56] References Cited

U.S. PATENT DOCUMENTS

| | | | |
|---|---|---|---|
| 4,121,099 | 10/1978 | French et al. | 250/296 |
| 4,234,791 | 11/1980 | Enke et al. | 250/281 |
| 4,300,044 | 10/1981 | Iribarne et al. | 250/282 |
| 4,730,111 | 3/1988 | Vestal et al. | 250/288 |
| 4,814,612 | 3/1989 | Vestal et al. | 250/288 |
| 4,883,958 | 11/1989 | Vestal | 250/288 |
| 4,902,891 | 2/1990 | Vestal | 250/281 |
| 4,999,493 | 3/1991 | Allen et al. | 250/288 |
| 5,070,240 | 12/1991 | Lee et al. | 250/288 |
| 5,115,131 | 5/1992 | Jorgenson et al. | 250/288 |
| 5,306,412 | 4/1994 | Whitehouse et al. | 250/288 |
| 5,306,910 | 4/1994 | Jarrell et al. | 250/288 |
| 5,349,186 | 9/1994 | Ikonomou et al. | 250/288 |

OTHER PUBLICATIONS

Article: "Interpreting Mass Spectra of Multiply Charged Ions," *Anal. Chem.*, vol. 61, pp. 1702–1708 (1989), by Mann et al.

Article: "Peptide and Protein Analysis by Electrospray Ionization–Mass Spectrometry and Capillary Electrophoresis–Mass Spectrometry,"*Analytical Biochemistry*, vol. 179, pp. 404–412 (1989), by Loo et al.

Article: "Small Volume and Low Flow–rate Electrospray Ionization Mass Spectrometry of Aqueous Samples," *Rapid Communications in Mass Spectrometry*, vol. 7, pp. 1017–1021 (1993), by Gale et al.

*Primary Examiner*—Jack I. Berman
*Assistant Examiner*—Kiet T. Nguyen
*Attorney, Agent, or Firm*—Browning Bushman

[57] ABSTRACT

Electrospray equipment and techniques are provided for receiving a liquid solution containing test molecules of interest and solvent and forming ionized droplets of interest for analysis by a mass spectrometer. The flow path within the electrically charged spray needle 16 may be filled with a packing material 20 for adsorbing selected chemicals in the liquid solution before being discharged from the spray needle into a vaporizing chamber 33. The spray needle preferably comprises a fused silica capillary tubing, and the discharge end 25 of the capillary tubing is spaced closely adjacent an exit orifice 31 of the vaporizer probe 12. Inert gas such as pure nitrogen is input to the probe. The techniques of the present invention are particularly well suited for mass spectrometer analysis of low flow rate test material.

30 Claims, 3 Drawing Sheets

ELECTROSPRAY METHODS AND APPARATUS FOR TRACE ANALYSIS

FIELD OF THE INVENTION

The present invention relates to electrospray techniques for producing ions suitable for chemical composition analysis. More particularly, this invention relates to improved techniques and apparatus for ionizing electrospray droplets containing molecules of interest and solvent for mass spectrometric analysis of various chemical compounds, wherein the test sample is comparatively small and/or high sensitivity is required.

BACKGROUND OF THE INVENTION

Mass spectrometry (MS) is a widely accepted analytical technique in the chemical sciences to obtain qualitative and quantitative information from a sample. MS is commonly used to determine molecular weight, identify chemical structures, and accurately determine the composition of mixtures. MS is becoming increasingly important in biological research to determine the structure of organic molecules based on the fragmentation pattern of ions formed when sample molecules are ionized.

A technique for focusing and declustering trace ions travelling into a vacuum chamber is disclosed in U.S. Pat. No. 4,121,099. A tandem quadrupole-based mass spectrometer for selected ion fragmentation studies is disclosed in U.S. Pat. No. 4,234,791. A technique for analyzing chemical compounds involving the formation of fine spray droplets of a solution containing the compound to be detected and electronically charging the spray droplets such that ionized molecules of interest is disclosed in U.S. Pat. No. 4,300,044. Techniques for vaporizing liquid solutions in order to detect physical or chemical properties of the samples are disclosed in U.S. Pat. Nos. 4,730,111 and 4,814,612. Relevant technical articles include Mann et al., "Interpreting Mass Spectra of Multiply Charged Ions," *Anal. Chem.*, Vol. 61, pp. 1702–1708 (1989); and Loo et al., "Peptide and Protein Analysis by Electrospray Ionization-Mass Spectrometry and Capillary Electrophoresis-Mass Spectrometry," *Analytical Biochemistry*, Vol. 179, pp. 404–412 (1989).

Electrospray ionization is similar in some respects to thermospray techniques. U.S. Pat. No. 4,883,958 discloses an improved interface for coupling liquid chromatography to solid or gas phase detectors involving thermospray vaporization. An improved thermospray vaporizer, and more particularly a vaporizer probe employing a reduced diameter nozzle, is disclosed in U.S. Pat. No. 4,902,891.

U.S. Pat. No. 4,999,493 and the references cited therein also disclose electrospray ionization techniques. Electrospray droplets are passed into an ion generating chamber that is maintained at a selected pressure. The walls of the ion-generating chamber are controllably heated at a temperature that will desolvate the droplets and produce ionized molecules of interest for analysis by the mass spectrometer. Electrospray (ES) ionization mass spectrometry is becoming widely used in the analysis of biological molecules, especially peptides and proteins. Continuous flow ionization has the capability of accurately measuring the masses of large proteins as well as small peptides and other organic molecules. ES can operate under variable solvent conditions, which allows the technique to be used as an interface for coupling various separation techniques, such as liquid chromatography (LC), to MS. Reverse phase LC can also be used to effectively desalt and concentrate a sample prior to its introduction into the mass spectrometer, which may be essential to the success of the ES analysis.

One of the most challenging applications of modern analytical technology in biological research requires the analysis of compounds such as endogenous metabolites and hormones at low femtomole concentrations and in microliter volumes of the solutions that contain relatively high salt concentrations. MS can be successfully employed on such samples and can provide analytical capabilities at the molecular level with high-mass measurement accuracy. The specificity of MS is further enhanced in the tandem MS mode. MS has proven to be essential in the neurosciences for monitoring physiologically active substances, such as neuropeptides. The majority of neuropeptide release studies have been performed by radioimmunoassay (RIA) or radioreceptorassay (RRA), which have desired sensitivity but lack specificity due to antibody-reactivity.

MS has been used to identify neuropeptides isolated from pooled brain tissues. After extensive chromatographic purification procedures, samples have been analyzed by fast-atom bombardment tandem MS with a detection sensitivity of approximately 50 pmol. Constant-infusion ES analysis of proteins has resulted in sensitivities in the range of 200 fmol/μL to 1 pmol/μL. ES ionization coupled to either LC or capillary zone electrophoresis (CZE) has greatly increased sensitivity for both peptides and proteins. Projection limits for peptides from LC-ES procedures are typically in the 100 to 500 fmol range. CZE-ES results show attomole sensitivity for the total amounts of analyte loaded, although because of low load volumes, sample solutions have to be relatively highly concentrated. Biological extracellular concentrations of neurosubstances are typically 4 to 6 orders of magnitude lower at the low attomole/μL level.

Various techniques are designed to accommodate less sample material. These techniques typically have high sensitivity but require loading of high concentration samples, which often are not readily available. An article by Gale et al. entitled "Small Volume and Low Flow-rate Electrospray Ionization Mass Spectrometry of Aqueous Samples," *Rapid Communications in Mass Spectrometry*, Vol. 7, pp. 1017–1021 (1993), discusses using proposals for accommodating low flow rate electrospray ionization analysis.

Improved techniques are thus required to take full advantage of electrospray capabilities, particularly for those instances where ultrahigh sensitivity is required or where the sample of interest from the chromatograph has a relatively low flow rate. The disadvantages of the prior art are overcome by the present invention, and improved techniques are hereinafter disclosed utilizing electrospray for improved ionization of molecules of interest to enhance the reliability and sensitivity of the mass spectrometric or other gas-phase analysis.

SUMMARY OF THE INVENTION

The micro-electrospray ionization technique of the present invention optimizes operation for ultrahigh sensitivity typically using nanoliter/minute flow rates. The back end of the probe is sealed, and pure dry nitrogen gas is used as a bath gas during ionization. A high voltage connection is made outside the probe shaft with a special connector. A voltage drop in the liquid solution within the capillary between the high voltage connection and the discharge end of the spray needle will desirably charge the solution at a level appropriate for electrospray, although the charge is applied to the liquid solution at a position substantially upstream from the discharge end of the capillary. The effluent or sample may be sprayed from a fused silica capillary tubing at comparatively low flow rates. The spray end of the capillary may be etched to optionally form a cone or tapered tip for reliable sub-microliter flow rates. The exit orifice of the probe may be a flat plate with a small diameter hole for droplets and ions to exit. The orifice in the flat plate is spaced very close to the discharge nozzle of the spray needle to maximize sensitivity.

The sample transfer capillary that terminates in the spray tip within the probe may be packed with a small diameter LC packing material for adsorbing appropriate chemical compounds. These compounds may be adsorbed from relatively large volumes, for example, in the range of from 10 to 100 µL, and may be desorbed in a narrow high concentration band by a one-step or gradient elution of solvent. Ultrahigh sensitivity is achieved by the combination of nanoliter/ minute flow rates, a narrow spray pattern, and micro LC-capillary spray tip to yield high concentration sample introduction. The use of a fused-silica capillary allows high voltage to be applied outside the spray nozzle area.

A micro-electrospray ionization source operates with nanoliter/minute flow rates and yields zeptomole or attomole per microliter sensitivity tier peptides. This source also yields attomole or femtomole per microliter sensitivity for proteins in the 70,000 molecular weight range. Those skilled in the art will appreciate that the sensitivity and mass measurement accuracy may be demonstrated with peptides using methionine-enkephalin (M-enk) and neurotensin (NT), and with proteins using apomyoglobin, carbonic anhydrase B, and bovine serum albumin. In addition, the coupling of micro-ES with MS/MS has been demonstrated. Desalting and concentration of dilute solutions may be accomplished by on-line nanoliter flow rate LC methods. According to the technique of the present invention, a desalting/concentration LC separation process may be an integral part of the source that is built into the spray needle. This feature eliminates dead volumes and carry-over to provide instantaneous delivery of compounds to the mass analyzer.

The micro-ES ionization source of the present invention has highly increased sensitivity compared to conventional electrospray techniques. The ionization source is optimized to accommodate nanoliter flow rates of from 10 to 800 nL/min, although flow rates slower or faster than those in this range may be achieved, and by spraying directly from a capillary needle that, for the analysis of peptides, contains C-18 liquid chromatographic packing as an integrated concentration desalting device. A total of 500 attomole of M-enk has been desorbed from a capillary column spray needle loaded as a 10 µL injection of 50 amol/µL solution. The mass spectrum showed the ion at a signal-to-noise (S/N) ratio of better than 4:1 chromatographic peak with a width of about 12 s. A narrow range tandem mass spectrum was obtained for M-enk from the injection of 500 amol, and a full-scan tandem mass spectrum was obtained from a 50 fmol. For proteins, the average mass measurement accuracy was approximately 100 to 200 ppm for the injection of 2.5 fmol of apomyoglobin and 20 to 40 ppm for 200 fmol. Carbonic anhydrase B and bovine serum albumin showed similar mass measurement accuracies.

It is an object of the present invention to improve the sensitivity performance of electrospray techniques, particularly where the solution is from low flow rate separation devices, such as CE, micro LC, microdialysis, or nanoliter-per-minute infusion processes. A related object of the invention is to provide greater capability for electrospray with nanoscale liquid chromatography or other chemical interactions occurring within the spray needle. According to the method of the invention, a chemical reaction between the liquid solution and a selected solid material occurs within the spray needle and desirably near the discharge from the spray needle.

According to another object of the invention, the micro-electrospray source can be used in analysis of many biological processes, more particularly where metabolites, neuropeptides, hormones, and similar substances are monitored at endogenous levels. The micro-electrospray source may be combined with a separation device, so that separation occurs as the sample passes along the spray needle to the discharge. For example, the technique of the present invention provides for the removal of salt from the analyte within the spray needle as an automated routine for sample injection. A selected chemical process occurs within the spray needle and preferably within 5 cm of the discharge from the spray needle to obtain extremely high sensitivity at very low flow rates.

It is a feature of the present invention to provide on-line sample desalting/concentration/purification with high flexibility and a zero dead-volume post-column design that maintain separation efficiency. The improved technique benefits by the placement of the spray needle within 5 mm of the nozzle orifice. The tip of the spray needle is accordingly placed as close to the source opening leading to the analyzer as practically possible to obtain the maximum transfer efficiency of the sample. By eliminating huge gas loads, pumping or vacuum problems in the mass spectrometer are minimized, thereby rendering micro ES suitable for magnetic sector, FTMS, and ion trap analyzers.

By making the ion source the reaction vessel, samples bound to needle packing can be made to react with various reagents or enzymes prior to desorbing and spraying into the mass spectrometer. Another advantage of the invention relates to reduction in the tendency of peptides in very low concentration to bind to the internal surfaces of capillaries and injection valves. To minimize this effect with analysis of dilute solutions of NT, the entire sample path including the fused-silica capillary and injector may be coated with another peptide. Also, blank injections between each NT sample may be analyzed and performed in order to verify that there is no significant carry-over from one sample to another. Various types of chemical processes may be effectively integrated into the spray needle.

These and further objects, features, and advantages of the present invention will become apparent from the following detailed description, wherein reference is made to the figures in the accompanying drawings.

DETAILED DESCRIPTION OF THE PREFERRED EMBODIMENTS

Figure 1:
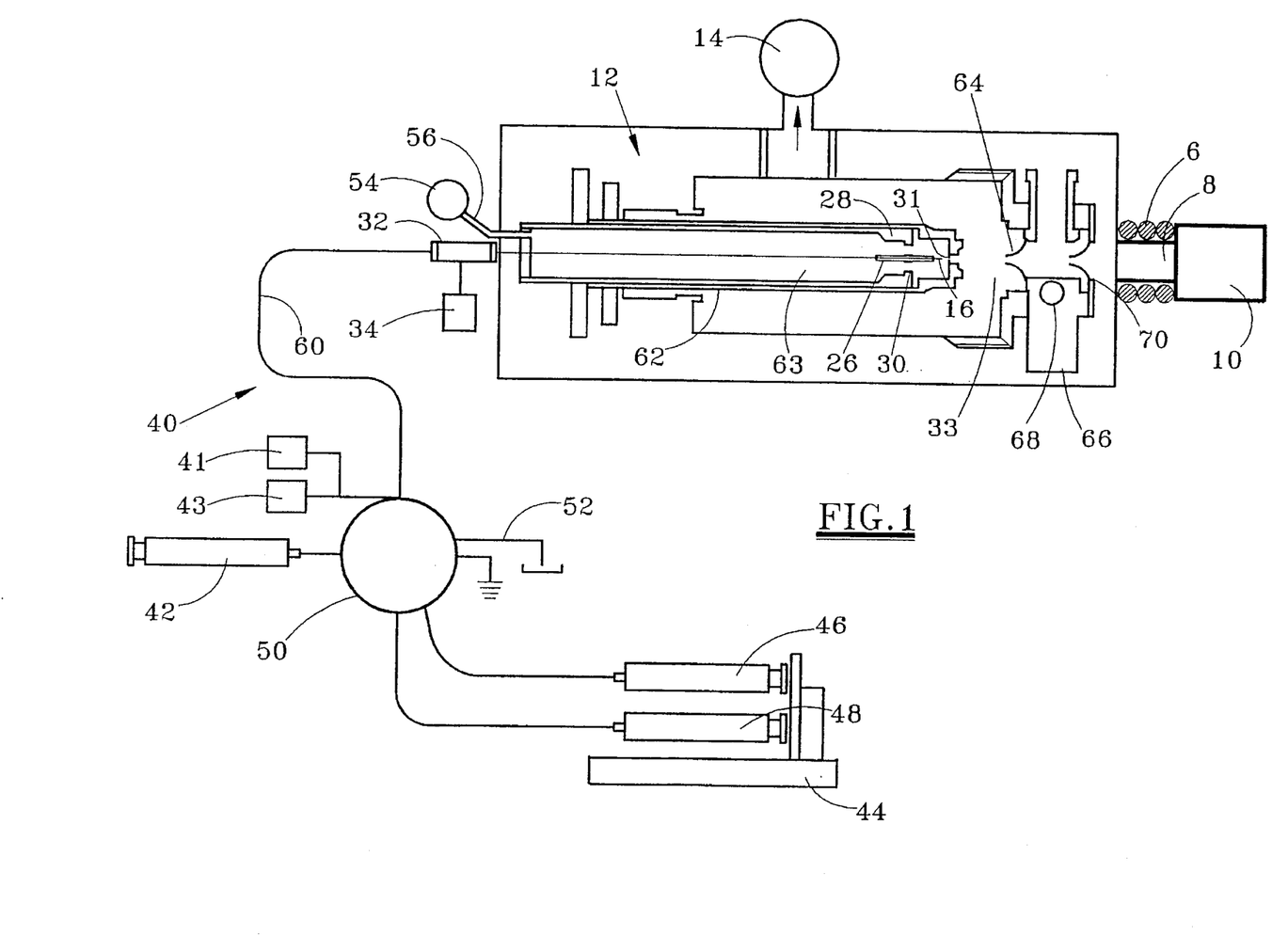
FIG. 1 illustrates a suitable source according to the present invention.

Mass spectra were obtained with a TSQ 70 triple-quadrupole mass spectrometer 10 (Finnigan-MAT, San Jose, Calif.)

with a 20 kV dynode and software updated to TSQ 700 status. The mass spectrometer included a conventional ion-generating chamber 8 and a heater 6 to desolvate droplets of interest within chamber 8 to produce molecules of interest. The pumping system was the original configuration that consisted of two Baizers (Baizers, Hudson, N.H.) TPH 330 turbomolecular pumps with the addition of a 590 L/min TriVac (Leybold-Heraeus, Export, Pa.) D25B rotary vane rough pump. The ES source 12 also had its own two-stage pumping system 14 that consisted of two 323 L/min Baizers UNO-016B rotary vane pumps. To reduce the volume of liquid flowing into the source, a small inner diameter capillary needle 16 was used. An ES source 12 was a modified PerSeptive Biosystems, Vestee Products, Houston, Tex., source, and is generally shown in FIG. 1. The modifications are discussed subsequently.

Figure 2:
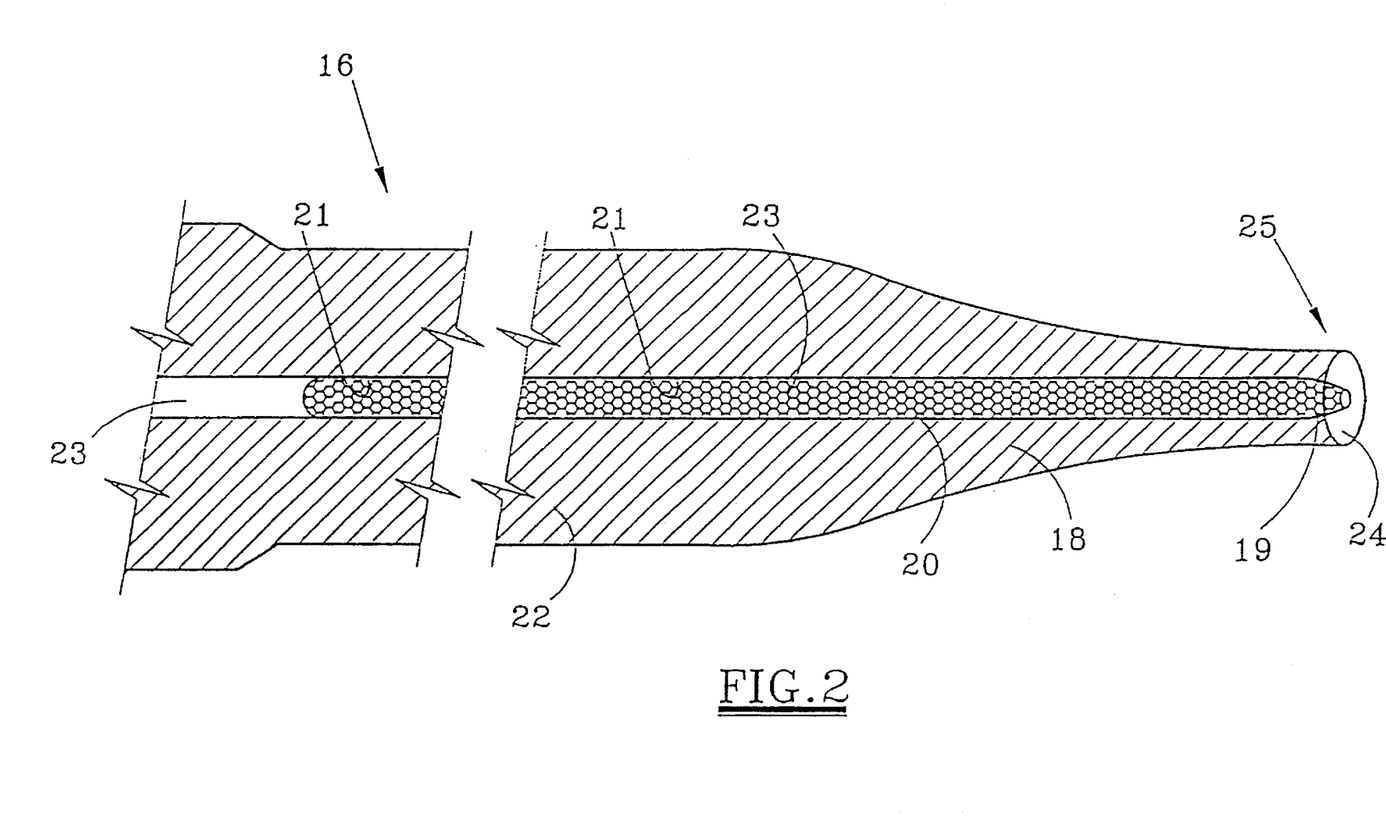
FIG. 2 illustrates the tip end of a suitable sample transfer capillary according to the present invention with a probe packed with LC packing material.

Spray needles or capillaries for accommodating nanoliter-per-minute flow rates were constructed from a fused silica capillary of 50 µm i.d. For the direct injection or infusion of peptides and proteins, capillary needles as shown in FIG. 2 were etched with HF to form tapered tips 18. For preconcentration and desalting of peptide samples, capillary needles were packed with reverse phase C-18/(10 µm) particle packing 23, as shown in FIG. 2. The capillary needles alternatively may be packed with a receptor material or an antibody material. Etching may not be critical, since unetched capillary needles appear to produce performance results similar to needles with tapered tips.

Needles 16 as shown in FIG. 2 were constructed from fused-silica capillary tubing (Polymicro Technologies, Phoenix, Ariz.) with inner diameters defining a substantially uniform flow path ranging from 5 to 250 µm. The main body 22 of each needle thus conforms to the cylindrical shape of the tubing. The polyamide coating was burned away from the tip (approximately 0.5 cm), and the tip was then lowered into a 49% solution of hydrofluoric acid (HF) while distilled $H_2O$ was pumped through the capillary at 500 nL/min. The progress of the etching was monitored with a microscope until a tapered needlelike tip 18 was obtained. The tip was then carefully ground by hand to a flat or planar end face 24 by using the flat side of a ceramic cutting stone. For preconcentration and desalting of peptide samples, unetched capillary needles were packed with reverse-phase C-18 (10-µm) particles as described below. The fused silica capillary body 22 had an approximately 220 µm o.d., and the o.d. of the face 24 tapered to ~75 µm. More importantly, the diameter of the exit hole of the spray needle is typically from 5 to 20 µm, depending upon the inner diameter of the flow path in the capillary. A very small diameter capillary thus may not need a restricted exit hole.

With reference to FIG. 1, the downstream end of the capillary 16 was supported by a PEEK (polyether ether ketone) sleeve 26 that was secured in the probe tip 28 by a hard rubber support 30. The opposite upstream end of the needle was attached to a stainless-steel zero dead-volume fitting 32 with a 0.5-mm through-hole. High voltage was applied by voltage source 34 to the electrically conductive fitting 32 and thus to solvent passing through the electrically non-conductive spray needle 16 at this union. Depending on experimental conditions, the voltage applied to the solution at the fitting 32 varied from 2.0 to 3.5 kV. The estimated voltage of the solution discharged from the spray needle would typically be 600 to 800 volts lower, depending upon solution conditions. Electrical current leakage to other components was insignificant because of the high resistance of the (~0.5 m long) capillary transfer line and by additional grounding of the switching valve and/or syringe pump discussed below. Voltages on the nozzle averaged between 200 and 250 V, and the repeller voltage was set to 10 V. Tandem mass spectra were produced by using argon gas in the collision cell at a pressure of 1.6 mtorr. The original conical nozzle in the Vestec source was replaced with a 0.4 mm through-hole flat nozzle 31.

Samples were introduced into the source 12 by constant infusion or direct injection via a valve-loop system 40, as shown in FIG. 1. Constant infusions were made by loading the sample into a 250 µL gas-tight Hamilton syringe 42. Alternatively, the samples may be received from a standard liquid chromatography unit 43 or a capillary electrophoresis unit 41. The sample was presented to the source at a rate of from 0.3 to 6.4 µL/min via a Harvard Apparatus (South Natick, Mass.) Model 2274 syringe pump 44. The pump 44 included an elute container 46 for delivering a 50% methanol, 0.25% acetic acid solution, and a load container 48 for delivering a 2% methanol, 0.25% acetic acid load. Loop injection was accomplished by using either a Rheodyne (Cotati, Calif.) 8125 injector valve with a 5 µL loop or, for column concentration, a Valco (Houston, Tex.) 10-port valve 50 equipped with a 10 µL loop. The valve 50 was equipped to discharge waste via discharge line 52. In both cases, a Harvard syringe pump equipped with Hamilton 250 µL syringes provided the solvent flow at 820 nL/min.

The original ES source did not employ counterflowing gas to help desolvate the sample, but did allow ambient air to aid in drawing the ions through the converging nozzle for discharge to the analyzer. This arrangement produced relatively high background signals in this environment, which were often sufficient to mask the signal of interest in high-sensitivity applications. This deficiency was remedied by making the probe gas tight and supplying the probe with ultra-pure dry $N_2$ at 970 mL/min (~1 atm) from source 54 via input line 56. While another inert gas could be used, nitrogen performs well and is relatively inexpensive.

When LC mass spectrometry methods were required for desalting or sample preconcentration, fused-silica capillaries with 50 µm i.d. and 220 µm o.d. were packed with the following modification. The capillary was cut into a 30 cm length, washed with 2-propanol, and dried with a stream of helium. Then the polyamide coating was burned away with a butane lighter (~0.5 cm), and the end of the capillary was tapped lightly into a vial containing a small amount of 5 µm spherical silica (SIL 120A-S5, YMC Corp., Morris Plains, N.J.). The amount of silica (~100 to 200 microns in length) pressed into the capillary was monitored with a stereoscope. With reference to FIG. 2, the silica frit was sintered in place with a butane microtorch, forming fused silica particles 19. The tip 18 of the capillary 16 was then ground by hand to a perpendicular flat end 24 with the flat side of a ceramic cutting stone. The grinding process was monitored under a stereoscope to form the desired spray needle discharge nozzle 25. For the preparation of capillary column needles, etching was not done because of the difficulty of maintaining the frit after etching.

To prepare packed needles, a slurry of 20 mg/mL C18 (10 µm spherical C-18 particles, ODS-AQ 120A S10, YMC Corp., Morris Plains, N.J.) in 100% methanol was prepared. The slurry was then poured into a brass packing bomb that contained a 1.9 cm-deep, 1.5 cm-diameter reservoir. A Teflon-coated miniature stirring bar kept the slurry uniform. Two high-performance liquid chromatography (HPLC) that protrude from the top of the bomb allow the connection of an HPLC pump (130A, Applied Biosystems Inc., Foster City, Calif.) on the inlet side and the column to be packed on the outlet side. The HPLC pump was used to pump 100% methanol into the packing bomb. A microscope was used to monitor the packing of the column. The column was packed slowly until a bed volume of 40 nL was obtained (2 cm in length). The length of the packed column was typically at least 50 times, and more preferably was from 100 to 500 times, the substantially uniform diameter of the flow path through the spray needle. The column was disconnected from the packing bomb, directly pressurized with 100% methanol to ~3500 lb/in.$^2$, and then flushed with and stored in 30% methanol until used.

For optimization of spray conditions, several capillary needles of various internal diameters were etched with HF to form tapered needles. Theses needles were tested with a constant infusion of 100 fmol/μL M-enk in 50% methanol that contained 0.25% acetic acid to optimize source voltages and flow rates at levels needed to maintain a steady spray. To measure the detection level of the source with each needle, a constant infusion of 10 fmol/μL M-enk solution in 50% methanol-0.25 % acetic acid was used.

A 50 μm i.d. of fused silica transfer line 60 connected the valve 50 with the source 12, as shown in FIG. 1. The source included a nylon probe shaft 62 that generally defines a probe chamber 63 therein. The source included a 0.6 mm, 10 V skimmer 64, a standard source block or repeller 66, a heater 68, and a columnator ground 70. The cavity 33 between the source nozzle 31 and the skimmer 64 is the vaporizer chamber. The tip of the spray needle 16 was preferably maintained very close to the source nozzle 31, i.e., preferably from 0.1 to 5 mm. A stage 2 pump (not shown) maintained a vacuum downstream from the skimmer at approximately 0.15 torr. The vacuum downstream from the columnator was maintained at ~$10^{-4}$ torr.

Table 1 shows that as the inner diameter of the capillary needle increases, the flow rate increases, and the minimum high voltage needed to establish a steady spray decreases. The high voltage values listed in Table 1 are the voltage values applied to the fitting 32.

TABLE 1

| Capillary Dimensions (μm) | | Flow Rate | High Voltage | Nozzle Voltage | Sensitivity with M-enk[1] |
|---|---|---|---|---|---|
| i.d. | o.d.[2] | (μL/min) | (kV) | (V) | (amol) |
| 20 | 140 | 0.30 | 3.5 | 250 | 125 |
| 20 | 350 | 0.30 | 3.5 | 250 | 125 |
| 50 | 220 | 0.82 | 3.5 | 250 | 342 |
| 50 | 350 | 0.82 | 3.5 | 250 | 342 |
| 100 | 350 | 1.15 | 3.0 | 273 | 479 |
| 200 | 350 | 1.64[3] | 2.4 | 238 | 683 |
| 250 | 350 | 2.29[3] | 2.2 | 228 | 954 |

[1]Amount of M-enk consumed from a constant infusion of 10 fmol/μL to produce spectra from five scans with an average S/N of 2.5 or better.
[2]Before etching. After etching, the wall thickness at the tip was ~ from 10 to 20 μm.
[3]Flow rates up to 6.4 μL/min were possible, but 10-fmol sensitivity was not obtained at the higher flow rates.

A stable spray could be established for 5- and 10-μm i.d. capillaries, although not as routinely as for larger diameter capillaries. The outer diameter of the capillary did not significantly affect the spray stability because each capillary had been etched to its minimal possible outer diameter (wall thicknesses were ~10 to 20 μm at the tip). The sensitivity (i.e., the amount of peptide needed to provide a spectrum with an S/N of 2.5 or better) increased as the inner diameter decreased and is a consequence of the decrease in flow rate with smaller inner diameter needles and consumption of less sample. For the experiments described below, selected needles had a 50 μm inner diameter because of their high sensitivity, low flow rate capability, and relative ease of use (capillaries with inner diameters of less than 20 μm were too susceptible to clogging by minute particulate matter to be of routine utility).

One of the most useful modes of operation for trace analysis of peptides and proteins is the direct injection of small volumes of analyte into a carrier solvent that continuously flows into the ES source. To provide preconcentration and desalting procedures, LC capability has been integrated into the micro-ES source. This was done by packing the needle with 10 μm C-18 particles to give an ~2 cm-long column at the tip of the spray needle, as described above. By spraying from the end of the column itself, all postcolumn dead volumes were eliminated.

Performance of the integrated LC-ES source was tested on several peptides, including M-enk, oxytocin, NT, and substance P. The performance of the micro-ES source was also tested in the tandem mass spectrometry mode. For peptides, sensitivities for "total amount injected" were in the zeptomole/attomole range, depending on the peptide. For proteins, sensitivities for "total amount injected" are in the attomole/femtomole range for apomyoglobin, carbonic anhydrase, and bovine serum albumin. For proteins, the average mass measurement accuracy was approximately from 100 to 200 ppm for the injection of 2 femtomoles and from 20 to 40 ppm for 200 femtomoles.

Figure 3:
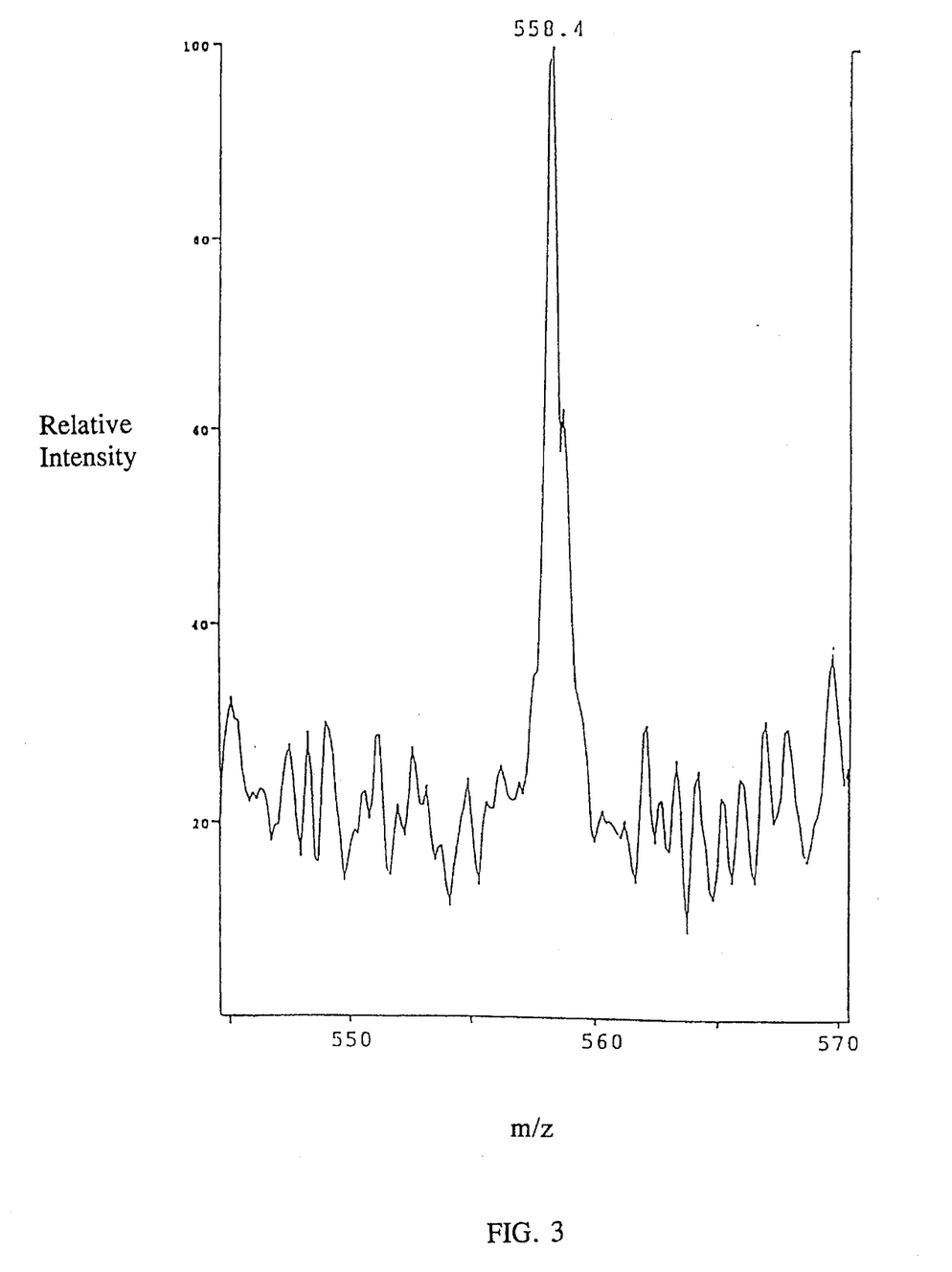
FIG. 3 graphically illustrates relative intensity as a function of m/z for direct injection of 10 µL of a solution of 320 zeptomoles/µL of neurotensin onto a C-18 packed micro-electrospray needle with subsequent elution by 50% methanol/0.25% acetic acid.

The replacement of ambient air with ultra-pure nitrogen as the flow-through gas in the ES probe had a dramatic effect on S/N measurements at low analyte levels. FIGS. 3a and 3b show the molecular (M+H)$^+$ ion species of met-enkephalin (M-enk) at 10 and 1 fmol (total) loaded on a column from solutions containing 1 fmol/μL and 100 attomoles/μL, respectively. Tests show that the spectrum obtained by using prepurified dry $N_2$ as compared with room air may have approximately 50-fold decreased background signal and an S/N of about 8:1 for m/z 574. A significant part of the sensitivity, or more precisely, the limit of detection enhancement, is the consequence of substantially decreased background chemical noise, which has been demonstrated for an injection of 100 fmol M-enk with both pure nitrogen and air as the bath gases. The highest sensitivity achieved was for the peptide NT.

This enhanced sensitivity similarly applies to MS/MS measurements. Good results were obtained from various peptides, including substance P and oxytocin. NT was the most sensitive peptide. Proteins can likewise be analyzed at high sensitivity with the source as disclosed herein. High sensitivity was obtained for peptides using M-enk or NT and was obtained for proteins using carbonic anhydrase or BSA as a test compound. If the sensitivity of the analysis according to conventional techniques is 1 fmol (total), the techniques of the present invention may utilize approximately 100 μL of sample containing 10 attomoles/μL concentration of analyte. Prior art methods such as CE may be sensitive at 1 fmol total, but require 0.01 μL of a 100 fmol/μL sample.

Apomyoglobin, carbonic anhydrase, and bovine serum albumin were used to test the performance of the micro-ES source with protein samples. For apomyoglobin, both the constant-infusion and direct-injection techniques were used to determine detection limits, whereas for carbonic anhydrase and serum album, only direct injection data are presented. The direct-injection method was preferred, although it is not as sensitive as constant infusion, because it allows discrete amounts of sample to be used and provides a situation more closely related to routine protein analyses.

Direct injections of two higher molecular weight proteins were also performed at or near the detection limits of the instrumentation to further test it capabilities. Reasonably accurate molecular weight measurements were obtained on injections of a total of low femtomole amounts of both carbonic anhydrase and bovine serum albumin.

Modifications to the ES source that allow its operation with solvent flow rates below 300 nL/min also allow the spray needle to be positioned much closer to the nozzle than in the conventional source. For the embodiment discussed above, the tip of the spray needle was about 2 mm from the nozzle 31. The decreased distance and low flow rate give a spray pattern of narrow dispersion, which allows more analyte to be drawn into the analyzer with less solvent.

The effect of the dry prepurified $N_2$ significantly decreased the background when the flat nozzle was used. The effect of the dry prepurified $N_2$ appeared to be most effective under conditions of high humidity. The increase in sensitivity occurs both with peptides and proteins and allows measurements on a few femtomoles of compound. Although a quadrupole analyzer was used in the present work, note that the characteristics of the micro-ES source would be advantageous for interfacing electrospray with a high voltage magnetic sector instrument. Low analyte concentrations coupled with low solvent flow rates greatly decrease source contamination and high voltage electrical discharge under normal (low salt) conditions.

Integrating micro-ES with reverse-phase C-18 capillary technology facilitates desalting and preconcentration of samples. The elution solvent (50% methanol-0.25% acetic acid) for peptides is also ideal for electrospray conditions, and by using the LC packing in the needle, post-column dead volumes are eliminated. The preconcentration-desalting capability also confers the practical advantage of allowing the source to handle quite dilute solutions. Thus, a 50 amol/μL ($5 \times 10^{-11}$M) peptide solution can be loaded in a 5 to 10 μL loop for direct injection. Other techniques such as capillary electrophoresis may be sensitive under specific conditions, but the low load volumes necessitate the use of much higher sample concentrations ($10^{-6}$ to $10^{-8}$M). This feature makes the micro-ES source ideal for certain applications where low flow rates and low concentration samples are produced. Microdialysis is an example of such a technique where the performance capabilities of micro-ES are an excellent match, providing on-line systems for dynamic chemical analysis from specific organs and tissues of live animals.

The techniques of the present invention allow small volumes of dilute solutions to be analyzed. For example, the direct injection of 10 μL of a solution containing 100 attomoles/μL of M-enk produced an $[M+H]^+$ ion at m/z 574.2 with an S/N ratio of greater than 5:1 obtained over a scan range of m/z 550-600. Sequence specific ions—e.g., the $A_4$ cleavage ion at m/z 397.5—were scanned in the MS/MS mode from the injection of 10 μL of M-enk from a 50 attomole/μL solution onto the packed needle column.

A recent approach has been aimed at measuring these neurosubstances in various substructures of rat brain at endogenous levels, estimated to be in the attomoles/μL range in dialysate, using a combination of microdialysis and mass spectrometry. The spray needle, a 22.5 cm length of 50 μm i.d. fused silica capillary containing an approximately 10 to 20 μm i.d. orifice and 1 cm of C-18 packing at the spray tip, was placed to within approximately 2 mm of the flat plate nozzle containing a 400 μm orifice to further optimize this electrospray source and thereby increase sensitivity for the specific analysis of neuropeptides.

In order to minimize the tendency of peptides in very low concentrations to bind to the internal surfaces of capillaries and injection valves during the analysis of dilute solutions of NT, the entire sample path, including the fused silica capillary and injector, was coated with another peptide. The walls of the substantially uniform flow path 23 within the spray needle 16 may thus have a peptide coating 21 thereon. This was done by continuously infusing 100 femtomole/μL of substance P, a peptide known to adhere relatively strongly to fused silica, for 30 minutes at a rate of 0.82 μL/min. Also, blank injections between each NT sample analyzed were performed in order to verify that there was no carryover from sample to sample.

Overall, this methodology provided an increased sensitivity for NT sufficient to give an S/N of 5:1 for the injection of 10 μL of a 320 zeptomole/μL solution of the peptide, or a total injection of 3.2 attomoles. Tests show that the peptide was desorbed off the stationary phase packing in the micro-ES needle by a 50% methanol/water solvent containing 0.25% acetic acid. Another benchmark for sensitivity that is often used is the amount of sample "consumed" in the time period required in producing a particular spectrum. In this constant infusion mode, a signal-to-noise (S/N) ratio of 3:1 was obtained for a spectrum of NT where 35 zeptomoles of this compound was consumed.

MS/MS capabilities are also important in measuring endogenous peptides because of the highly structure-specific nature of the analysis. These results represent the highest sensitivity achieved to date with this instrument. Significantly improved results were obtained by using a peptide that gives an abundant signal by electrospray, using water solutions (not physiological salt solutions), and scanning relatively narrow mass ranges. For dialysate samples from live animals, for example, one could expect a lower overall detection limit for NT of about 30 attomoles (total injected). This technique provides a benchmark for the level of sensitivity that can be achieved under optimal conditions.

According to this invention, the micro-ES source 12 uses a fused silica capillary needle to transmit samples from the high voltage connection 32 to the vaporizer chamber 33. The capillary 32 terminates in the spray tip 18, which is within the chamber 33 and closely adjacent the exit orifice 31, i.e., from 0.1 to 5 mm and preferably less than 3 mm. This arrangement allows for various capillary separation devices to be easily and effectively integrated into this needle.

One arrangement allows an LC packing material as discussed above to be placed in the needle to achieve an LC based separation. This packing is typically from 5 to 10 μm diameter particles that may be coated with C-18, ion exchange resin, or may be uncoated beads of desired chemical adsorbing material. Such packing allows for preconcentration, desalting and separation of compounds in the sample. Flow rates are low, typically from 50 to 800 μL/min. Because of close proximity of the spray needle to the source nozzle 31 hole, efficiency above 90% of sample transfer to the mass spectrometer is achieved. Another arrangement uses a wall-coated capillary to achieve this preconcentration, desalting and separation requirement. The coating 21 is of a desired adsorbing material, and serves a function similar to the packing discussed above.

A selected solid material may be placed within the flow path of the needle for causing chemical reactions to occur within the liquid solution while flowing through the spray needle. The solid material may thus be an activated surface on small beads, a polymeric substance, proteins or antibodies. Immobilized enzymes or other catalysts that hydrolyze proteins and peptides to smaller fragments may be placed within the spray needle to alter chemical groups on these molecules. The solid material placed within the flow path will be selected dependent upon the desired chemical reaction with the liquid solution passing through the spray needle, e.g., desalting, hydrolysis, separation, concentration or purification. Also, the term "solid material" as used herein is intended to mean any material which is not swept away by the liquid solution, and includes waxes and gels which may be applied to the interior walls of the spray needle or to beads placed within the flow path of the spray needle.

In order to obtain the desired high sensitivity, it is important that the selected solid material which is placed within the flow path of the needle for chemically reacting with the liquid solution be positioned so that it is closely adjacent the discharge end of the spray needle. As shown in FIG. 2, the selected solid material, e.g., the beads 23, are ideally positioned within the downstream portion of the needle and preferably as close as is practical to the discharge end of the needle. The selected solid material should be placed within 5 cm of the discharge end of the needle, and preferably within 3 cm of the discharge end of the needle, to minimize diffusion and mechanical mixing prior to discharge from the spray needle. It is also important that the high voltage be applied to the liquid solution substantially upstream from the discharge end of the spray needle rather than at the needle discharge. This arrangement leads to a relatively narrow spray path, and allows the exit orifice of the probe to be spaced closely adjacent to the discharge nozzle of the spray needle, i.e., from 0.1 to 5 mm and preferably less than 3 mm, to reduce losses.

Yet another arrangement uses a capillary electrophoresis (CE) device so that the needle 16 is a micro-electrospray source. By placing high voltage on the sample introduction end of this capillary with source 34 as shown in FIG. 1, compounds are able to separate electrophoretically along the needle 16, and may then be sprayed directly into the mass spectrometer. For this application, the high voltage source 34 as shown in FIG. 1 may subject the upstream end of the needle 16 to a voltage of from 25 to 35 kV. This CE capillary separation may be of the open or gel filled type, and the discharge end of the capillary may be appropriately filled. The electrospray probe may surround the terminal end of the needle, including the tip. Due to the voltage drop along the needle, capillary zone electrophoresis creating separation within each sample will occur within the capillary tube as discrete samples are sequentially passed through the needle 16 by controlling injector valve 50 as shown in FIG. 1. The high voltage applied to the upstream end of the capillary should be at least 8 kV. The capillary length and the liquid solution conditions must be controlled to result in a voltage drop within the solution along the capillary so that the discharge end of the spray needle is at a nominal voltage of from 2.0 kV to 5.0 kV to produce the desired spray of solution. A makeup solution flow may be employed to achieve proper spray conditions. A downstream ground 70 within the source 12, one or more skimmers 64 and the applied voltage from source 34 thus achieve initial electrophoresis separation within the needle 16 and then physical separation of compounds within the downstream chamber of source 12. Depending on voltage applied, the length of the capillary needle could be adjusted to achieve the required voltage drop to achieve stable spray conditions. This arrangement could be operated with or without sheath flow.

Still another arrangement would involve the use of a 2-dimensional capillary separation, i.e., an LC/CE arrangement terminating at the needle to achieve a spray into the mass spectrometer. For example, a capillary LC may be connected to a CE capillary through a valveless transverse flow connection. The valveless LC/CE coupler may then be subjected to a high voltage. A sample may be injected into the micro-LC capillary using a standard sample injector. A spray of ions will be discharged from the tip end of the needle. This arrangement allows LC-type separation followed by (for each electing LC peak) a coupled electrophoretic separation.

The method according to the present invention is suggested by the above description. Ionized droplets including test molecules of interest and solvent may be obtained by providing a system as disclosed above. The exit orifice of the vaporizer probe is positioned from 0.1 to 5 mm from a discharge nozzle of a spray needle, and preferably less than about 3 mm from the discharge nozzle of the spray needle. The liquid solution is transmitted to the vaporizer chamber through a flow path in a spray needle, and the solution is discharged as droplets of interest into the vaporizer chamber. A high voltage is applied to the liquid solution, preferably outside the probe, so that a desired voltage is obtained at the discharge end of the spray needle to achieve electrospray. According to the method of the invention, a chemical reaction occurs within 5 cm of the discharge nozzle of the spray needle between a solid material and the liquid solution. The chemical reaction occurring within the spray needle may comprise adsorption of a selected chemicals within the liquid solution by positioning an adsorbing material within the flow path through the needle. Alternatively, the interior walls of the flow path and the spray needle may be provided with a coating to separate selected chemicals while passing through the spray needle.

Accordingly, various capillary separation devices or selected solid materials resulting in other chemical interactions with the liquid solution may be integrated into the micro-ES source. Purifying, concentrating, desalting, separating and hydrolysis are each considered chemical reactions which may occur within the needle to enhance sensitivity and structural information. The specific arrangement of this source is ideally suited to effectively integrate the micro-ES source and various chemical processes occurring within the capillary to minimize diffusion and mechanical mixing. Dead volumes downstream from the chemical process are thus effectively eliminated, resulting in minimum band spreading.

Various types of gas phase and solid phase detectors may be used with the techniques of the present invention. The foregoing disclosure and description of the invention is illustrative and explanatory thereof, and various changes in the size, shape, and materials, as well as in the details of the illustrated construction, may be made within the scope of the appended claims without departing from the spirit of the invention.

What is claimed is:

1. Apparatus for receiving a liquid solution containing test molecules of interest and solvent and for forming ionized droplets of interest for test analysis of the molecules of interest, comprising:

a vaporizer chamber for receiving the ionized droplets of interest;

a spray needle having a flow path therein for transmitting the liquid solution to the vaporizing chamber, the spray needle having a discharge nozzle for discharging the ionized droplets of interest into the vaporizer chamber;

a charging source for electrically charging the liquid solution to obtain an electrospray discharge from the spray needle; and a selected solid material within the flow path of the needle for chemically interacting with the liquid solution while passing through the spray needle.

2. The apparatus as defined in claim 1, wherein the selected solid material comprises:

an adsorbing material within the flow path of the spray needle for adsorbing selected chemicals in the liquid solution.

3. The apparatus as defined in claim 2, wherein the adsorbing material provided within the flow path is a packing material.

4. The apparatus as defined in claim 1, wherein the selected solid material is a catalyst for chemically altering a compound within the liquid solution while passing through the spray needle.

5. The apparatus as defined in claim 1, wherein the selected solid material is positioned within 5 cm of the discharge nozzle of the spray needle.

6. The apparatus as defined in claim 1, wherein the spray needle comprises a fused silica capillary tubing having a substantially uniform flow path diameter therein of from 5 to 250 μm, and wherein the selected solid material is spaced axially along the flow path of the needle at least 50 times the diameter of the flow path.

7. The apparatus as defined in claim 6, wherein the end of the spray needle is etched to form a tapered tip.

8. The apparatus as defined in claim 1, further comprising:

a vaporizer probe having a probe chamber therein for receiving the spray needle; and the vaporizer probe including an exit orifice, the exit orifice being spaced about 0.1 mm to about 5 mm from the discharge nozzle of the spray needle.

9. The apparatus as defined in claim 1, further comprising:

a vaporizer probe having a probe chamber for receiving the spray needle; and a nitrogen source for inputting nitrogen gas to the probe chamber.

10. The apparatus as defined in claim 1, wherein the vaporizer chamber is in communication with a mass analyzer for test analysis of the ionized droplets of interest.

11. The apparatus as defined in claim 10, wherein the mass analyzer comprises:

an ion generator chamber downstream from the vaporizer chamber; and a heater to desolvate the droplets of interest within the ion generating chamber and thereby produce ionized molecules of interest.

12. The apparatus as defined in claim 1, wherein the test molecules of interest are output from a liquid chromatography unit to the spray needle.

13. Apparatus for receiving a liquid solution containing test molecules of interest and solvent and for forming ionized droplets of interest for test analysis by a mass spectrometer including an ion-generating chamber and a heater to desolvate droplets of interest within the ion-generating chamber and thereby produce ionized droplets of interest, the apparatus comprising:

a vaporizer chamber in communication with the ion-generating chamber for receiving the droplets of interest;

a spray needle having a flow path therein for transmitting the liquid solution to the vaporizing chamber, the spray needle having a discharge nozzle for discharging the droplets of interest into the vaporizer chamber, the flow path in the spray needle having a substantially uniform flow path diameter upstream from the discharge nozzle;

charging means for electrically charging the liquid solution;

a selected adsorbing material within the flow path in the spray needle for adsorbing selected chemicals;

a vaporizer probe having a probe chamber for receiving the spray needle; and a dry gas source for inputting purified gas to the probe chamber.

14. The apparatus as defined in claim 13, further comprising:

the vaporizer probe including a flat plate exit orifice, the flat plate exit orifice being spaced from about 0.1 mm to about 5 mm from the discharge nozzle of the spray needle.

15. The apparatus as defined in claim 13, wherein the needle comprises a fused silica capillary tubing having a substantially uniform flow path diameter therein of from 5 to 250 μm, and wherein the selected solid material is spaced axially along the flow path of the needle at least 50 times the diameter of the flow path.

16. Apparatus for receiving a liquid solution containing test molecules of interest and for forming ionized droplets of interest for test analysis by a mass spectrometer including an ion-generating chamber, the apparatus comprising:

a vaporizer chamber in communication with the ion-generating chamber for receiving the droplets of interest;

an electrically non-conductive spray needle having a flow path therein for transmitting the liquid solution to the vaporizing chamber, the spray needle having a discharge nozzle for discharging the droplets of interest into the vaporizer chamber;

charging means for electrically charging the liquid solution upstream from the discharge nozzle; and a vaporized probe including an exit orifice, the exit orifice being spaced from less than 5 mm from the discharge nozzle of the spray needle.

17. The apparatus as defined in claim 16, further comprising:

a selected solid material within the flow path in the spray needle for chemically reacting with the liquid solution while passing through the spray needle.

18. The apparatus as defined in claim 17, wherein the selected solid material comprises:

a selected adsorbing material within the flow path of the spray needle for adsorbing selected chemicals in the liquid solution.

19. The apparatus as defined in claim 17, wherein the selected solid material is positioned within 5 cm of the discharge nozzle of the spray needle.

20. The apparatus as defined in claim 17, wherein the selected solid material is provided along the flow path in the spray needle over an axial spacing of more than 100 times a diameter of the flow path.

21. The apparatus as defined in claim 16, wherein:

the charging means applies a high voltage of at least 8 kV to the liquid solution in an upstream end of the spray needle for creating a voltage drop within the solution along the spray needle to create capillary electrophoresis of the sample within the spray needle.

22. The apparatus as defined in claim 21, further comprising:

the charging means applies a sufficient voltage to the solution such that the capillary electrophoresis occurs immediately upstream from the discharge nozzle of the spray needle; and the electrically non-conductive spray needle is a fused silica spray needle.

23. A method of forming ionized droplets including test molecules of interest for test analysis of the molecules of interest, the method comprising the steps of:

providing a vaporizer chamber;

transmitting a liquid solution including the test molecules of interest to the vaporizing chamber through a flow path within a spray needle;

discharging the liquid solution as droplets of interest into the vaporizer chamber;

electrically charging the liquid solution while transmitting the liquid solution to the vaporizing chamber through the flow path within the spray needle; and creating a chemical reaction with 5 cm of a discharge nozzle of the spray needle between a solid material and the liquid solution while passing through the spray needle.

24. The method as defined in claim 23, further comprising the step of:

providing an adsorbing material within the spray needle to separate selected chemicals while passing through the spray needle.

25. The method as defined in claim 23, further comprising the step of:

spacing an exit orifice of a vaporizer probe from about 0.1 mm to about 5 mm from the discharge nozzle of the spray needle.

26. The method as defined in claim 23, further comprising the step of:

coating interior walls of the flow path in the spray needle to separate selected chemicals while passing through the spray needle.

27. The method as defined in claim 23, further comprising the steps of:

providing an ion-generating chamber downstream from the vaporizer chamber;

heating the droplets of interest within the ion-generating chamber to produce ionized molecules of interest; and analyzing the ionized molecules of interest by mass spectrometry.

28. The method as defined in claim 23, further comprising the steps of:

positioning the spray needle within a probe chamber of a vaporizer probe; and inputting pure nitrogen gas to the probe chamber.

29. The method as defined in claim 23, wherein the step of electrically charging the liquid solution includes the step of applying a voltage of from 2.0 kV to 5.0 kV to the liquid solution.

30. The method as defined in claim 23, further comprising the step of:

heating the droplets of interest to desolvate the droplets and form ionized molecules of interest.

* * * * *

UNITED STATES PATENT AND TRADEMARK OFFICE
CERTIFICATE OF CORRECTION

| | | |
|---|---|---|
| PATENT NO. | : 5,572,023 | Page 1 of 1 |
| APPLICATION NO. | : 08/453385 | |
| DATED | : November 5, 1996 | |
| INVENTOR(S) | : Richard M. Caprioli | |

It is certified that error appears in the above-identified patent and that said Letters Patent is hereby corrected as shown below:

In Column 8, lines 31-34, delete the entire sentence "FIGS. 3a and 3b show the modecular (M+H) + ion species of met-enkephalin (M-enk) at 10 and 1 fmol (total) loaded on a column from solutions containing 1 fmol/uL and 100 attomoles/uL, respectively".

In Column 8, line 44, after "NT" insert --as shown in Fig. 3--.

Signed and Sealed this

Twenty-ninth Day of January, 2008

JON W. DUDAS
*Director of the United States Patent and Trademark Office*